(12) United States Patent
Hirst

(10) Patent No.: US 12,274,528 B2
(45) Date of Patent: *Apr. 15, 2025

(54) COMMUNICATION BUS

(71) Applicant: Drägerwerk AG & Co. KGaA, Lübeck (DE)

(72) Inventor: Michael D. Hirst, Webster, MA (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/092,522

(22) Filed: Jan. 3, 2023

(65) Prior Publication Data

US 2023/0147450 A1 May 11, 2023

Related U.S. Application Data

(63) Continuation of application No. 16/954,784, filed as application No. PCT/US2018/065990 on Dec. 17, 2018, now Pat. No. 11,564,573.

(60) Provisional application No. 62/599,951, filed on Dec. 18, 2017.

(51) Int. Cl.
| | |
|---|---|
| A61B 5/00 | (2006.01) |
| G06F 9/48 | (2006.01) |
| G06F 9/54 | (2006.01) |
| H04L 12/40 | (2006.01) |

(Continued)

(52) U.S. Cl.
CPC .......... *A61B 5/0022* (2013.01); *A61B 5/0024* (2013.01); *G06F 9/4881* (2013.01); *G06F 9/54* (2013.01); *H04L 12/40143* (2013.01); *H04L 12/4641* (2013.01); *H04L 67/12* (2013.01)

(58) Field of Classification Search
CPC ..... H04L 67/125; H04L 67/025; H04L 67/02; H04L 67/10; H04L 12/4641; H04L 67/12; H04W 4/80; H04W 4/70; G06F 9/54; G06F 9/4881

See application file for complete search history.

(56) References Cited

U.S. PATENT DOCUMENTS

| | | | |
|---|---|---|---|
| 9,148,483 B1* | 9/2015 | Molettiere | ............ H04L 67/535 |
| 2009/0303883 A1* | 12/2009 | Kucharczyk | .......... H04L 49/351 |
| | | | 370/241 |

(Continued)

*Primary Examiner* — Lan Dai T Truong
(74) *Attorney, Agent, or Firm* — NOLTE LACKENBACH SIEGEL

(57) ABSTRACT

Systems, apparatuses, and methods are described herein for a communication bus that virtualizes physiological data. Sensors and/or physiological data acquisition devices have different physical connectors which provide physiological data from a patient to a shared interface such as a display or patient monitor. A transfer interface within a mount can receive and interpret data streams associated with one or more physiological data acquisition devices. The transfer interface can prioritize the various data streams associated with the one or more physiological data acquisition devices and generate a single, combined data stream based on the assigned prioritization. The transfer interface can provide the combined data stream for transmission to a patient monitor via an interchangeable transport medium. Another transfer interface can process and/or virtualize the data streams from the physiological data acquisition devices.

19 Claims, 11 Drawing Sheets

(51) Int. Cl.
*H04L 12/46* (2006.01)
*H04L 67/12* (2022.01)

(56) References Cited

U.S. PATENT DOCUMENTS

| | | | | |
|---|---|---|---|---|
| 2011/0225303 | A1* | 9/2011 | Engebretson | H04L 47/193 709/227 |
| 2012/0082036 | A1* | 4/2012 | Abedi | H04W 84/18 370/329 |
| 2013/0064102 | A1* | 3/2013 | Chang | H04L 49/70 370/255 |
| 2015/0070187 | A1* | 3/2015 | Wiesner | G16H 40/67 340/870.02 |
| 2016/0197820 | A1* | 7/2016 | Götz | H04L 47/125 370/236 |

* cited by examiner

COMMUNICATION BUS

TECHNICAL FIELD

The subject matter described herein relates generally to a virtual communication bus mirroring a physical communication bus.

BACKGROUND

Patient monitoring systems are essential medical devices providing vital physiological data to clinicians for care of patients which presents challenges for inside as well as outside the hospital environment. A number of sensors and/or physiological data acquisition devices can be used to obtain and/or monitor physiological data of a patient. The sensors and/or physiological data acquisition devices can have a number of varying data connectors and/or signals. A shared interface such as a display monitor or patient monitor can be used to process and visually provide the physiological data of the patient to medical personnel. The shared interface can also be interconnected with a docking station. The docking station can have additional devices and/or cables coupled thereto such as a hospital network connection, storage devices, bar code readers, device power supplies, and the like. In addition to the numerous connections to the docking station, each sensor and/or physiological data acquisition device also requires a physical connection to the display or patient monitor. Such physical connections can affect the placement or inhibit movement of the monitor in a patient environment by requiring large amounts of real estate within the patient environment. Additionally, the physical connections can be cumbersome to the medical personnel utilizing the monitor as the physical connections can require physical disconnection from the monitor in order to relocate one or more of the sensors and/or physiological data acquisition devices.

A multi-pin connector can be used to connect the various data connectors. The multi-pin connector can be a purely mechanical/electrical connector having no processing capabilities. Processing capabilities to interpret data from the sensors and/or physiological data acquisition devices can be required in both a monitor and a corresponding docking stations. This dual processing can lead to data latency and/or data integrity concerns. The multi-pin connector can also be cumbersome and/or time consuming to clean due to the intricate cable connections of varying types. Electrical isolation of each connector to meet various patient and/or user safety standards is often accomplished using discrete isolation for each connector. Additionally, difficulties with mechanical alignment between the multi-pin connector and the various data connectors can also cause the connector to age and lose effectiveness of data transmission over time.

SUMMARY

In one aspect, a system for use with a first physical device and a second physical device configured to provide data relating to a patient via a first data stream and a second data stream respectively includes a mount module having a first input port configured to be coupled to the first physical device and a second input port configured to be coupled to the second physical device. The mount module is configured to (i) receive the first data stream via the first input port and the second data stream via the second input port and (ii) generate a prioritized data stream comprising the first data stream and the second data stream that is based on a priority level assigned to both of the first physical device and the second physical device. The system also includes a patient monitor configured to receive the prioritized data stream via a single data connection and to split the prioritized data stream into virtual representations of the first data stream and the second data stream. The virtual representations emulate operational characteristics of the first physical device and the second physical device. The system also includes an interchangeable transport medium module between the mount module and the patient monitor configured to transport the prioritized data stream via the single data connection.

In some variations, the first data stream includes physiological data derived from the patient and the second data stream includes non-physiological data. The priority level can be assigned to the first physical device is higher than the priority level assigned to the second physical device.

In other variations, an operating system can perform assignment of the priority level to the first physical device and the second physical device. In some variations, the first physical device is a Universal Serial Bus (USB) 0 device or a USB1 device.

In other variations, the mount module can include a first transfer interface configured to emulate operational characteristics of the first data stream received at the first input port and the second data stream received at the second input port by translating the first data stream and the second data stream into compatible signal representations for transport using the interchangeable transport medium.

In some variations, the operational characteristics can include at least one: device signals, control lines, or protocols within the first data stream and the second data stream.

In other variations, the first transfer interface can be configured to generate the prioritized data stream based on the priority level.

In some variations, the mount module can further include a multiplexer configured to queue the first data stream and the second data stream for generation of the prioritized data stream.

In other variations, the patient monitor can include a second transfer interface configured to split the prioritized data stream into the virtual representations.

In some variations, the second transfer interface can be configured to process the virtual representations of the first data stream and the second data stream, and generate a prioritized response data stream based on the priority level.

In other variations, the mount module can further include a de-multiplexer configured to deque the prioritized response data stream into a first response data stream and a second response data stream.

In some variations, the first physical device can be an Ethernet device configured to communicate with a hospital data network.

In other variations, the first physical device and the second physical device can include at least one of a Universal Serial Bus (USB) 0 device, a USB1 device, an Ethernet device, a flash drive device, a Subscriber Identification Module (SIM) device, or a general purpose input/output (GPIO) device.

In some variations, the interchangeable transport medium can include at least one of an optical link, a wired link, or a wireless link. In other variations, the interchangeable transport medium can include a virtual local area network.

In some variations, the first physical device can include one or more sensors coupled to the patient. In other variations, the first physical device can be a physiological data acquisition device coupled to the patient.

In another aspect, an apparatus for use with a first physical device, a second physical device, and a patient monitor, the first physical device and the second physical device being configured to provide data relating to a patient via a first data stream and a second data stream respectively includes a mount module having a first input port coupled to the first physical device and a second input port coupled to the second physical device. The mount module is configured to (i) receive the first data stream and the second data stream and (ii) generate a prioritized data stream comprising the first data stream and the second data stream that is based on a priority level assigned to the first physical device and the second physical device. The apparatus also includes an interchangeable transport medium module between the mount module and the patient monitor configured to transport the prioritized data stream via the single data connection. The patient monitor is configured to receive the prioritized data stream via a single data connection and split the prioritized data stream into virtual representations of the first data stream and the second data stream. The virtual representations emulate operational characteristics of the first physical device and the second physical device.

In another aspect, a method for implementation by a system as described herein include receiving, by the mount module, the first data stream from the first physical device. The mount module also receives the second data stream from the second physical device. The mount module generates the prioritized data stream including the first data stream and the second data stream that is based on the priority level assigned to both of the first physical device and the second physical device. An interchangeable transport medium transports the prioritized data stream via the single data connection. The patient monitor receives the prioritized data stream via the single data connection. The patient monitor splits the prioritized data stream into virtual representations of the first data stream and the second data stream. The virtual representations emulate operational characteristics of the first physical device and the second physical device.

The details of one or more variations of the subject matter described herein are set forth in the accompanying drawings and the description below. Other features and advantages of the subject matter described herein will be apparent from the description and drawings, and from the claims.

The subject matter described herein provides many technical advantages. For example, use of the subject matter herein can provide a virtual communication bus to a monitor that reflects physical connections to a mount. Using a virtual communications bus to transport the physiological data, the physical connections of the various sensors and/or monitoring devices can be centralized at a single location on a mount. Virtualizing physical connections of the sensors and/or patient monitoring devices can increase mobility of the display or patient monitor within a patient environment. For example, a shared interface such as a monitor can be moved around a patient environment having minimal or no physical connections preventing movement without having to disconnect cables to facilitate such movement. Additionally, use of the subject matter described herein can simplify a patient monitoring environment by allowing for a patient monitor to be mounted at an orientation of either 0 or 180 degrees with respect to a docking station. With use of the subject matter herein, data integrity of patient data is improved and data latency is reduced. Additionally, with use of the communication bus herein, electrical isolation can be achieved using a reduced number of electrical isolation points.

BRIEF DESCRIPTION OF THE DRAWINGS

Like reference symbols in the various drawings indicate like elements.

DETAILED DESCRIPTION

Patients that are admitted to a healthcare facility can require continuous physiological monitoring. This continual physiological monitoring can be a data intensive task that usually occurs no matter where the patient is located within the facility and can require a number of sensors and/or physiological data acquisition devices attached to the patient. Each sensor and/or physiological data acquisition device can have different physical connectors which provide physiological data from a patient to a shared interface such as a display or patient monitor. The virtualization of these connections can provide physiological data to the display or patient monitor. In turn, the display or patient monitor can be less restricted in movement about the patient environment (e.g., patient hospital or examination room).

Figure 1:
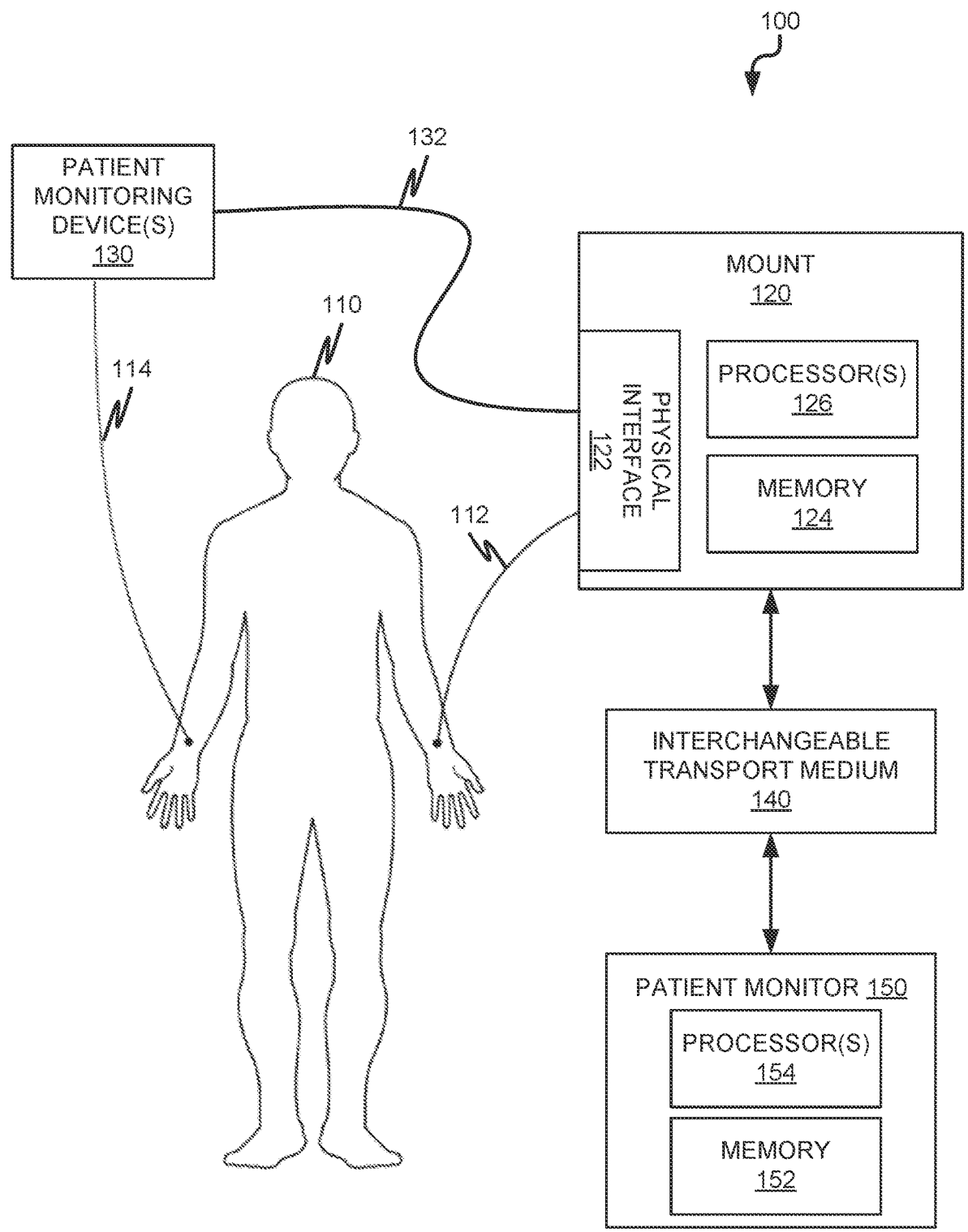
FIG. 1 depicts an example patient environment having a virtual communication bus.

FIG. 1 depicts an example patient environment 100 having a virtual communication bus. Within patient environment 100, physiological data of a patient 110 can be monitored by one or more sensors 112, 114. One or more sensors 112 can be coupled to a mount 120 via physical interface 122 to provide physiological data of patient 110. One or more sensors 114 can also be coupled to one or more patient monitoring devices 130 which may process and/or further provide physiologic data to mount 120 (e.g., via cable 132 coupling together one or more patient monitoring devices 130 and mount 120). Mount 120 can include memory 124 for storing instructions for execution by one or more processor/processor cores 126. Memory 124 can also be capable of storing data. Mount 120 can act as a proxy (e.g., facilitates exchange of data) between either patient 110 or the one or more patient monitoring device(s) 130 and transport physiological data via interchangeable transmit medium 140 to a patient monitor 150. Patient monitor 150 can render visual information that corresponds to the physiological data of patient 110 and provide a central location for data processing of the various data streams generated from one or more sensors 112,114 and/or patient monitoring device(s) 130. Patient monitor 150 can be rotatable by approximately 180 degrees about a vertical axis. Memory 152 can be included within display for storing instructions for execution by one or more processor/processor cores 154. Memory 152 can also be capable of storing data.

Figure 2:
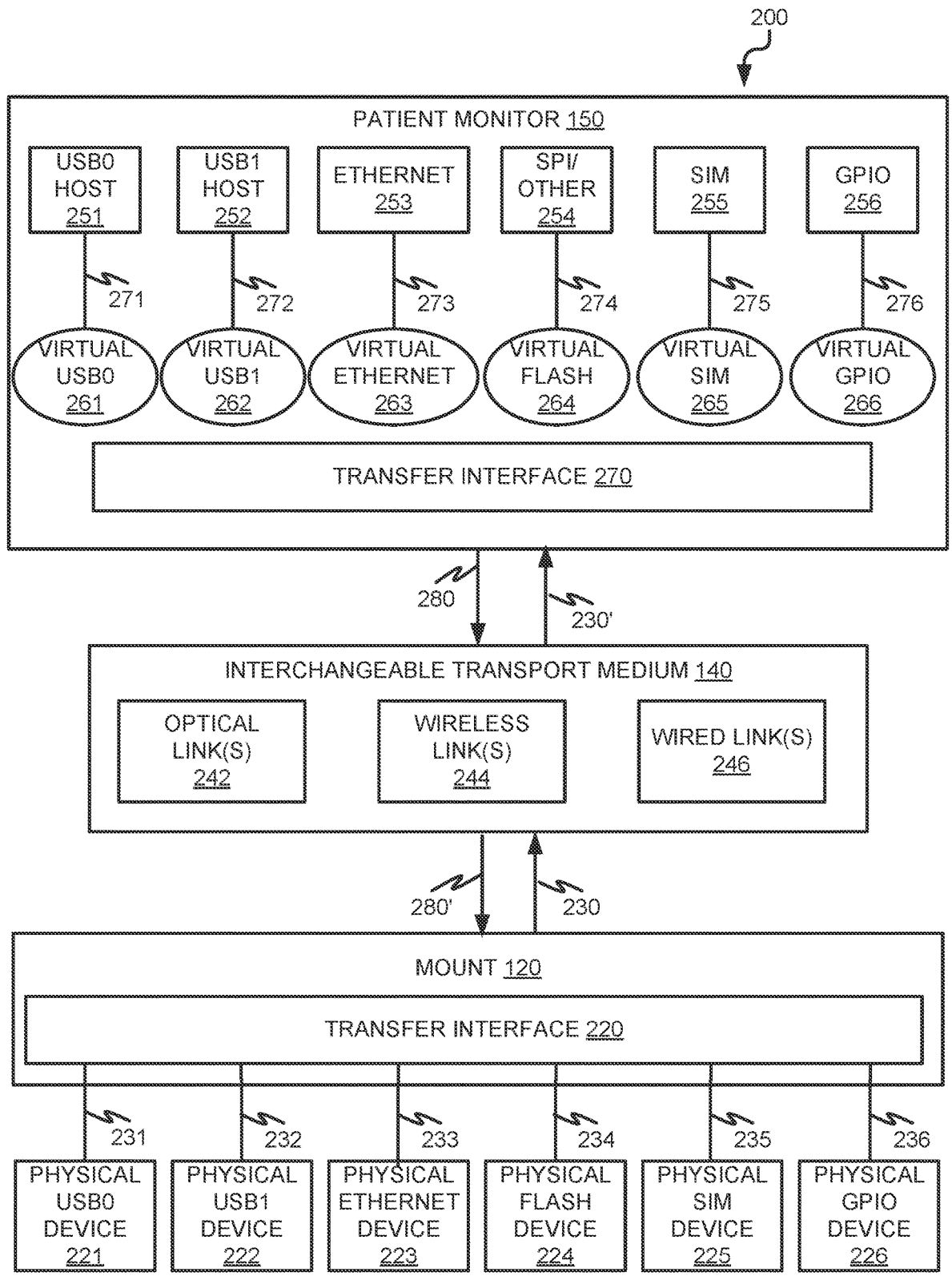
FIG. 2 depicts an example system architecture illustrating virtual communication of physiological data of patient.

FIG. 2 depicts an example system architecture 200 illustrating virtual communication of physiological data of patient 110. One or more physical input devices can be coupled to mount 120 (e.g., via physical interface 122 of FIG. 1). Physical input devices can include, but are not limited to, physical Universal Serial Bus (USB) 0 device 221, physical USB1 device 222, physical Ethernet device 223, physical flash storage device 224, physical Subscriber Identification Module (SIM) device 225, or other general purpose input/output (GPIO) devices 226. Each of the one or more physical input devices transmit data streams 231, 232, 233, 234, 235, 236 to transfer interface 220. Transfer interface 220 can include one or more software device drivers for the operation and/or control of the physical input devices. In some variations, the software device drivers can have a one-to-one correlation with each physical input device. In other variations, a single software device driver can interface with two or more of the physical input device interfaces depending upon the various communication protocols associated with a particular physical input device. The software device drivers can access the physical input devices. In some variations, transfer interface 220 may not include processing capabilities to analyze and/or process the data within data streams 231, 232, 233, 234, 235, 236 within mount 120. Instead, transfer interface 220 can utilize software device drivers to translate the data streams 231, 232, 233, 234, 235, 236 for transmission to patient monitor 150 which in turn can have such processing capabilities as described in more detail below.

Transfer interface 220 can be stored within memory 124 and have programming instructions that can be executed by one or more processor/processor cores 126. Transfer interface 220 can emulate operational characteristics of data (e.g., device signals, control lines, and/or protocols within data streams 231, 232, 233, 234, 235, 236). More specifically, the emulation of data streams 231, 232, 233, 234, 235, 236 can be compatible with a type of interchangeable transport medium 140 (e.g., optical link(s) 242, wireless link(s) 244, wired link(s) 246). A quality of service (QOS) mechanism within transfer interface 220 can monitor each data stream of the one or more physical input devices 221, 222, 223, 224, 224, 226 in order to protect the integrity of transfer interface 220 from an intermittent, malfunctioning, or non-operational physical input device. A priority is assigned by transfer interface 220 to each physical input device. Based on the priority, data stream 230 can be generated by transfer interface 220. Data stream 230 includes the emulated data from each physical input device assembled within a single data stream based on the assigned priority. The priority can be a priority stored within one or more processors of mount 120 and patient monitor 150. A higher priority can be assigned to the one or more physical input devices 221, 222, 223, 224, 224, 226 providing physiological data. A lower priority can be assigned to the one or more physical input devices 221, 222, 223, 224, 224, 226 not providing physiological data. For example, the data streams associated with physical USB0 device 221 and physical USB1 device 222, and corresponding virtual devices USB0 261 and USB1 262, can be given higher priority than other physical devices 223, 224, 225, 226 or virtual devices 263, 264, 265, 266. The higher priority assigned to physical USB0 device 221 and physical USB1 device 222 can be based on the transport of physiological data across those physical devices. In some variations, assignment of priorities to tasks can be managed by operating systems that execute on processors 126 and 154. For example, the tasks that are associated with USB devices 221, 222 and corresponding virtual devices 261, 262 may be given higher priority than other tasks, as they can be involved with the transport of physiological data.

Data stream 230 is transmitted to interchangeable transport medium 140 and subsequently transmitted to patient monitor 150 via output data stream 230'. Output data stream 230' remains substantively the same as data stream 230 with, in some variations, minor data formatting modifications based on the interchangeable transport medium 140. Interchangeable transport medium 140 can include one or more of optical link(s) 242, wireless link(s) 244 (e.g., Bluetooth, Wifi), or wired link(s) 246. Data stream 230' can be transmitted to patient monitor 150.

An example interchangeable transport medium 140 (e.g., optical link(s) 242, wireless link(s) 244, or wired link(s)) can include one or more virtual local area networks (VLAN). The one or more physical input devices 221, 222, 223, 224, 224, 226 can provide an interface for mount 120 to communicate with a data network, such as a hospital data network, via an RJ-45 or other Ethernet connection. The one or more physical input devices 221, 222, 223, 224, 224, 226 can provide direct connectivity between the data network and one or more processors of patient monitor 150, for example, via a first VLAN (e.g., VLAN1). A connection via a data network, such as a hospital network, can provide network traffic to and from patient monitor 150. In some examples, such a connection can have a rate-limited throughput to minimize or avoid bandwidth consumption between patient monitor 150 and mount 120. The rate-limited throughput can be controlled by an Ethernet switch (not shown) within mount 120 positioned between one or more physical input devices 221, 222, 223, 224, 224, 226, optical link 342, and one or more processor/processor cores within mount 120. Additionally, one or more processor/processor cores of mount 120 and one or more processor/processor cores of patient monitor 150 can transfer data using a second VLAN (e.g., VLAN2) that is included in an interchangeable transport medium (e.g., optical link(s) 242, wireless link(s) 244, or wired link(s)). In this example, VLAN2 can be a private network for remote device data for any of the one or more physical input devices 221, 222, 223, 224, 224, 226. Use of two VLANs in this example (e.g., VLAN1 and VLAN2) can improve data integrity of patient data and reduce data latency by prioritizing transport of physiological data between the patient monitor 150 and mount 120 with minimal to no data throttling.

Transfer interface 270 can be stored within memory 152. One or more processor/processor cores 154 can carry out various operations as described herein. Having similar characteristics as transfer interface 220, transfer interface 270 can unpack data stream 230' back into individual virtual devices that reflect the one or more physical devices (e.g., virtual devices 261, 262, 263, 264, 265, 266). Data stream 230' can be unpacked based on the priority queuing within data stream 230'. Each virtual device can have a one to one correlation with the physical input device for which it is emulating data. For example, virtual devices 261,262,263, 264,265,266 can emulate data of real data (e.g., device signals, control lines, and/or protocols) of physical input device 221, 222, 223, 224, 225, 226, respectively.

Patient monitor 150 can have one or more input ports configured to receive data from various connector types. For example, the one or more input ports can accept various physical input connectors including, but not limited to, USB0 host 251, USB1 host 252, Ethernet 253, Serial Peripheral Interface (SPI) 254, SIM cards 255, or other GPIO connections 256. Each virtual device emulating data can provide data to a corresponding input port as if a physical connector was coupled to the port. In other words, each of the one or more input ports 251, 252, 253, 254, 255, 256 receives data as if physical input device such as one or more physical input devices 221, 222, 223, 224, 225, 226 was coupled thereto. The physical wiring can be virtualized into emulated data streams 271, 272, 273, 274, 275, 276. For example, virtual devices 261, 262, 263, 264, 265, 266 provide emulated data streams 271, 272, 273, 274, 275, 276 of real data streams 231, 232, 233, 234, 235, 236 of physical input devices 221, 222, 223, 224, 225, 226, respectively.

In some variations, transfer interface 270 can include processing capabilities to analyze emulated data streams 271, 272, 273, 274, 275, 276. In such variations, mount 120 provides interface processing of data streams 231, 232, 233, 234, 235, 236 via one or more software device drivers within transfer interface 220. Patient monitor 150 provides data processing capabilities via transfer interface 270. Such a variation can reduce latency associated with data replication in both patient monitor 150 and mount 120. Additionally, such a variation can improve data integrity as the physical data acquisition devices (e.g., one or more physical input devices 221, 222, 223, 224, 224, 226) can be directly accessed at mount 120.

Depending upon needs of patient 110, one or more commands can be provided to patient monitor 150 via an interactive graphical user interface (e.g., via a mouse click on patient monitor 150, touch on a touch sensitive surface of patient monitor 150). For example, the commands can be provided back to corresponding physical input devices 221, 222, 223, 224, 225, 226. In response to receiving a command via patient monitor 150, one or more input ports 251, 252, 253, 254, 255, 256 can feed back data to one or more virtual devices 261, 262, 263, 264, 265, 266. The feedback data streams of each virtual device 261, 262, 263, 264, 265, 266 can be assigned a priority by transport interface 270. Based on the priority, transport interface 270 can assemble a single feedback data stream 280. Feedback data stream 280 can be transmitted to interchangeable transport medium 140. Feedback data stream 280' can be substantively similar to feedback data stream 280 with minor modifications necessary based on the type of interchangeable transport medium 140. Mount 120 can receive feedback data stream 280'. Transfer interface 220 can unpack feedback data stream 280' based on the various priorities of each data stream. Individual data streams correlating to the one or more physical input devices can be provided back by transfer interface 220.

Figure 3:
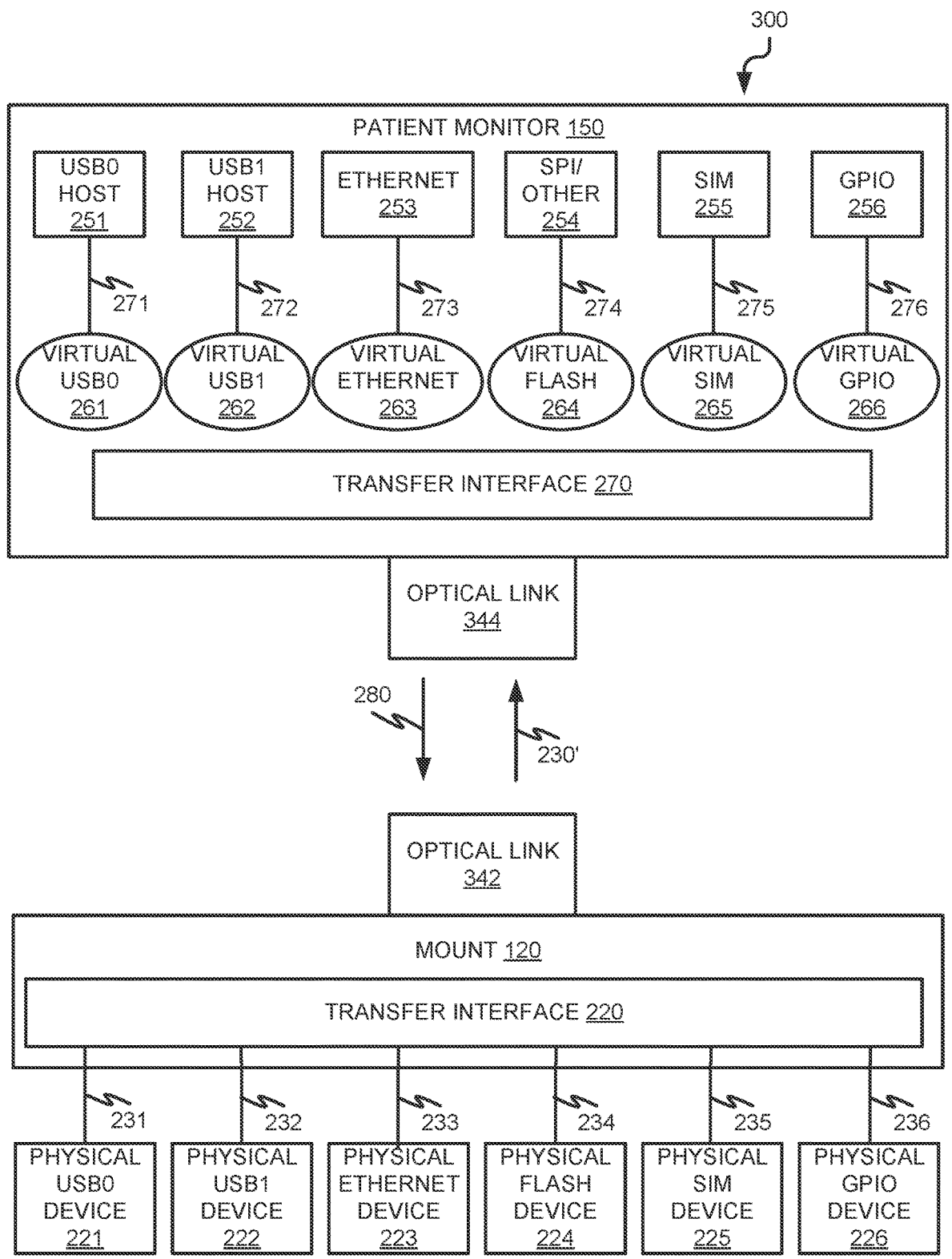
FIG. 3 depicts an example system architecture illustrating virtual communication of physiological data of patient using optical link(s)

FIG. 3 depicts an example system architecture 300 illustrating virtual communication of physiological data of patient 110 using optical link(s) 242. In one example, interchangeable transport medium 140 can include optical link(s) 242. Optical link(s) 242 can be coupled to mount 120 (e.g., optical link 342) and to patient monitor 150 (e.g., optical link 344). An airspace gap can separate optical link 342 and optical link 344 from each other. Data stream 230' can be transmitted over such airspace gap.

Figure 4:
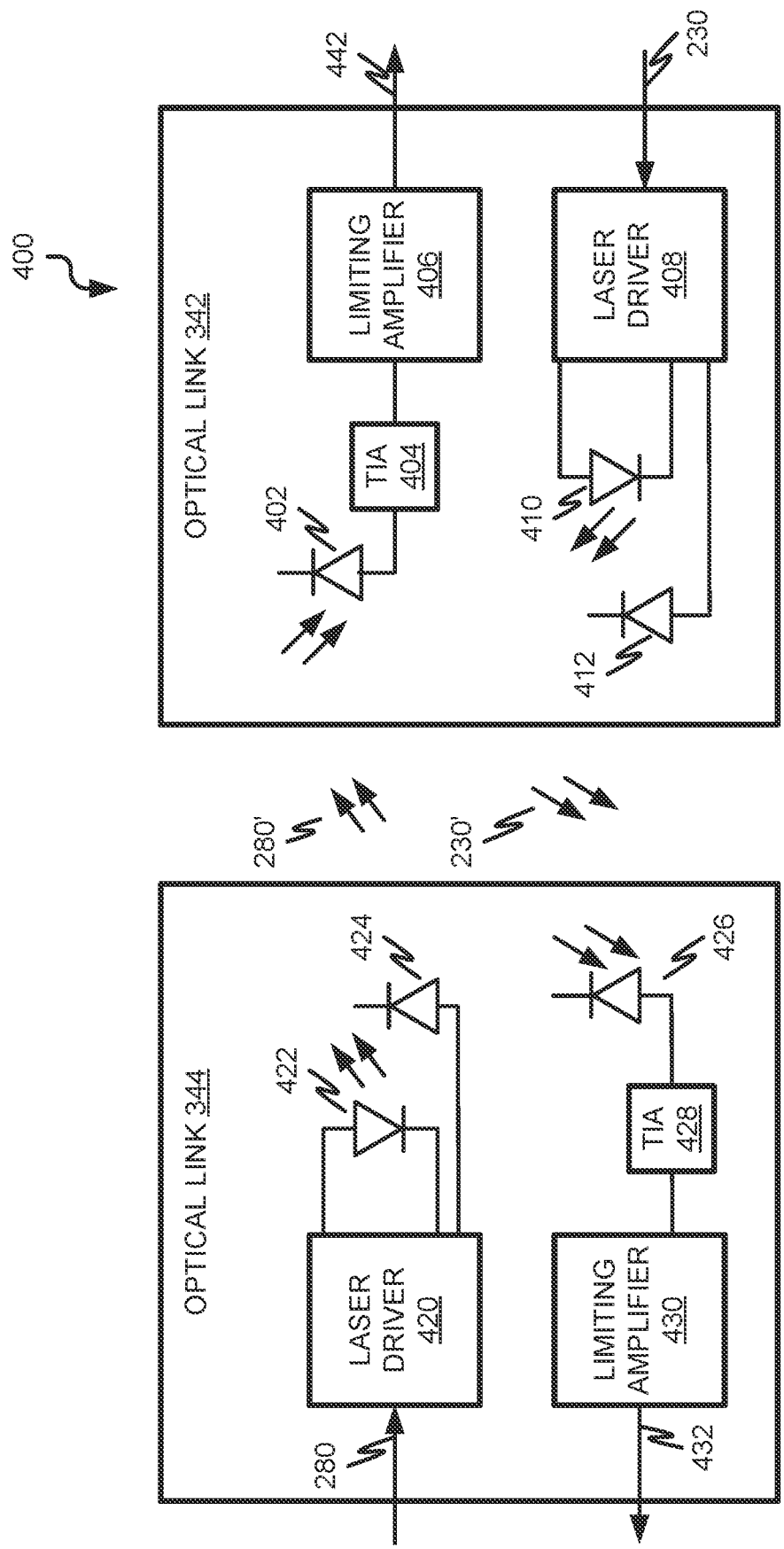
FIG. 4 depicts an example optical link block diagram further illustrating an example optical link.

FIG. 4 depicts an example optical link block diagram 400 further illustrating an example optical link. Optical link 342 can include photo diode (PIN) 402, Trans Impedance Amplifier (TIA) 404, limiting amplifier 406, laser driver 408, laser diode 410, and monitor diode 412. Optical link 344 can include laser driver 420, laser diode 422, monitor diode 424, PIN 426, TIA 428, and limiting amplifier 430.

Optical link 342 can receive data stream 230 from mount 120. Laser driver 408 and laser diode 410, coupled together, output an optical data stream (e.g., data stream 230') substantively to data stream 230. Data stream 230' is transmitted over an air gap (e.g., approximately 2 cm) to optical link 344. Monitor diode 424 can be a photo detector diode that monitors and/or detects laser pulses transmitted from optical link 342 to optical link 344. PIN 426 can be coupled to TIA 428 and receives data stream 230' identified by monitor diode 424. TIA 428 amplifies current within data stream 230' and provides it to limiting amplifier 430. Limiting amplifier 430 provides differential output signal 432 to patient monitor 150 for virtualization by transfer interface 270.

Feedback data can be generated by one or more input ports. For example, feedback data stream 280 can be provided by patient monitor 150 to optical link 344, as previously described. Laser driver 420 and laser diode 422, coupled together, can generate feedback data stream 280'. Feedback data stream 280' can be transmitted over an air gap (e.g., approximately 2 cm) to optical link 342. Monitor diode 412 can be a photo detector diode that monitors and/or detects laser pulses transmitted from optical link 344 to optical link 342. Feedback data stream 280' can be received by PIN 402 of optical link 342. TIA 404 amplifies current within data stream 280' and provides it to limiting amplifier 406. Limiting amplifier 406 provides differential output signal 442 to mount 120 for unpacking by transfer interface 220.

Figure 5:
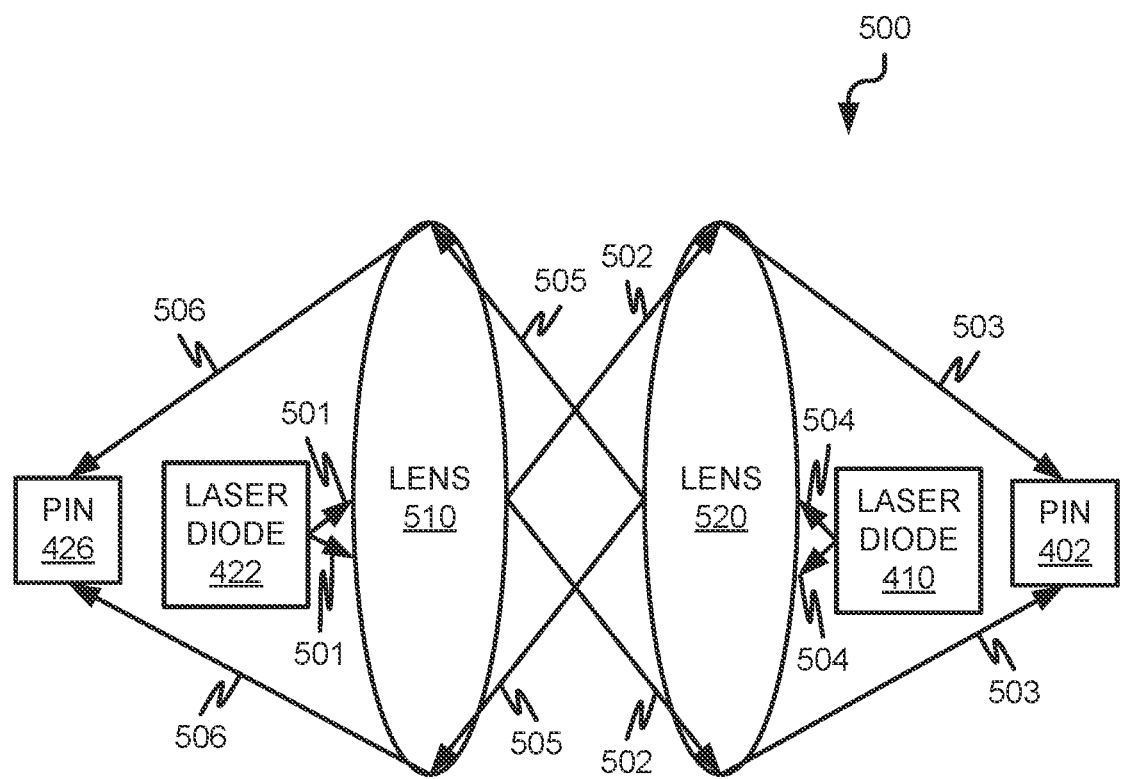
FIG. 5 depicts an example block diagram illustrating a lens system having bidirectional optics.

FIG. 5 depicts an example block diagram illustrating a lens system 500 having bidirectional optics. To support rotation of patient monitor 150 of approximately 180 degrees, lens 510 and lens 520 facilitate the optical data transmission of optical links 342 and 344. As illustrated in FIG. 5, laser diodes 410, 422 can be placed in front of PINs 402,426 when lenses 510, 520 are used to focus optical data. Optical waves 501 emitted by laser diode 422 can be directed through lens 510 to points on lens 520 (e.g., optical waves 502). Optical waves 502 reflect down to PIN 402 via optical waves 503. Similarly, optical waves 504 emitted by laser diode 410 can be directed through lens 520 to points on lens 510 (e.g., optical waves 505) which reflect down to PIN 426 via optical waves 506.

Figure 6:
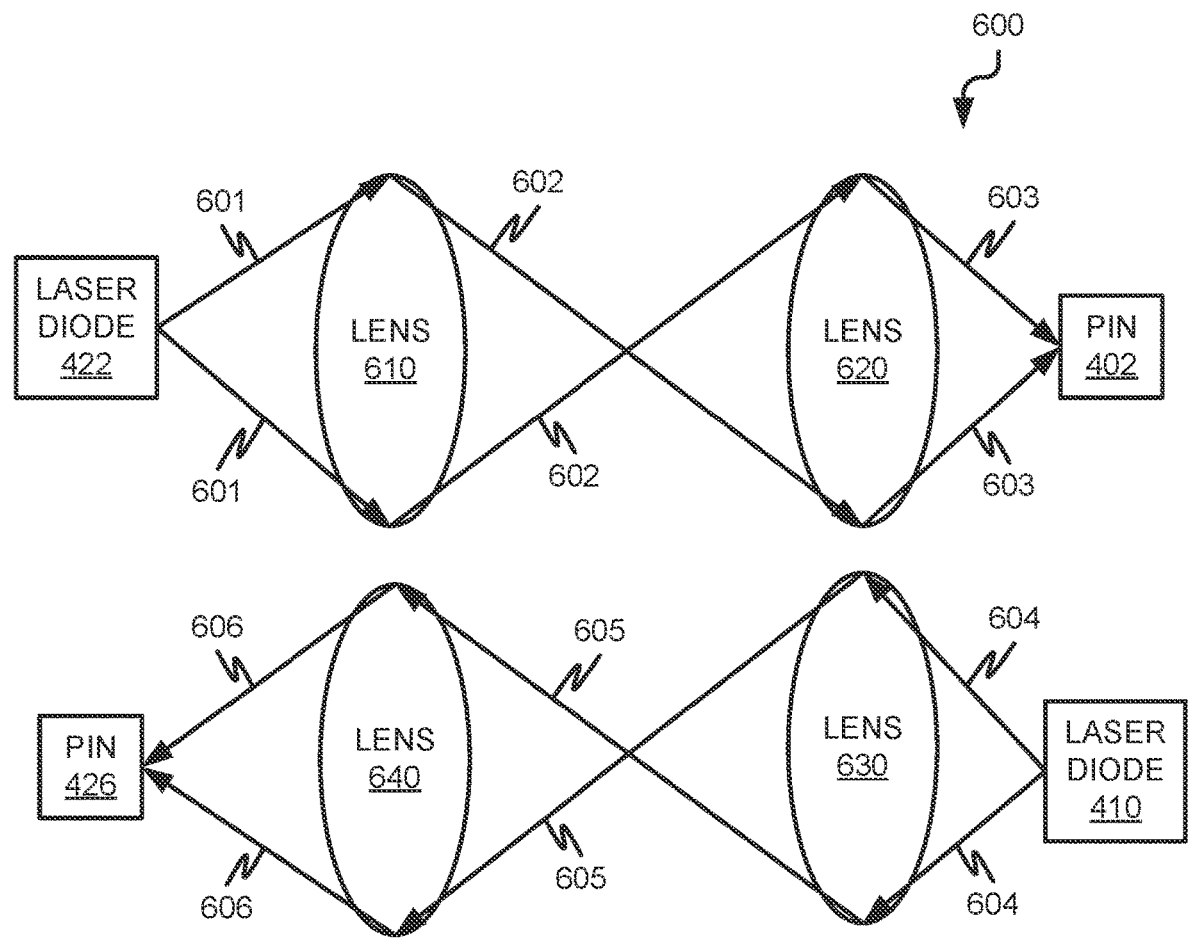
FIG. 6 depicts another example block diagram illustrating a lens system having unidirectional optics.

FIG. 6 depicts another example block diagram illustrating a lens system 600 having unidirectional optics. Laser diode 422 can emit optical waves 601, which reflect off lens 610. Lens 610 inverts the reflection of optical waves 601 to opposite sides of lens 620 (e.g., via light waves 602). Optical waves 603 are directed from lens 620 to PIN 402. Similarly, laser diode 410 can emit optical waves 604, which reflect off lens 630. Lens 630 inverts the reflection of optical waves 604 to opposite sides of lens 640 (e.g., via optical waves 605). Optical waves 606 are directed from lens 640 to PIN 426.

Figure 7:
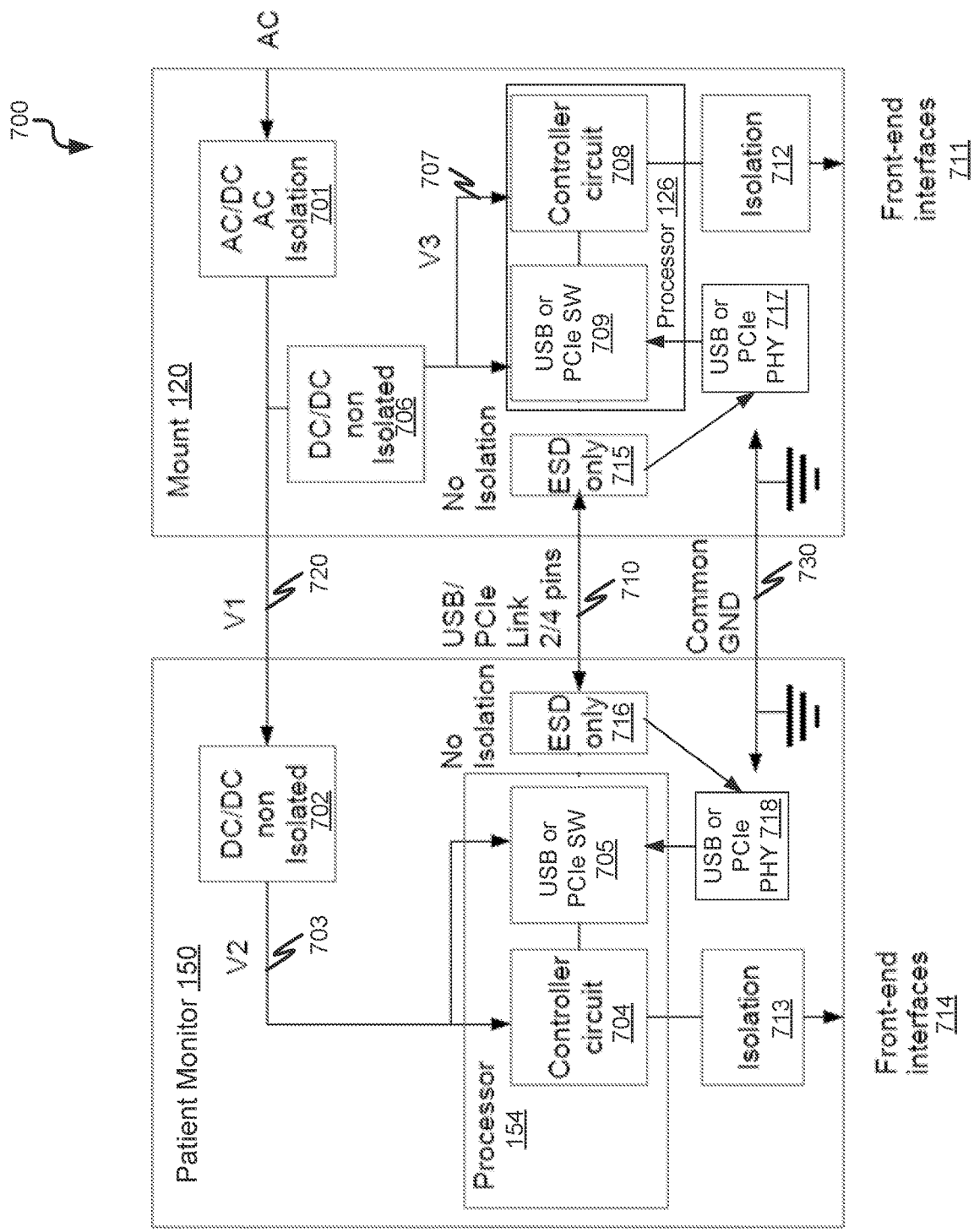
FIG. 7 depicts an example block diagram illustrating an example wired link(s)

FIG. 7 depicts an example block diagram 700 illustrating an example wired link(s) 246. Wired link(s) 246 can include a USB/Peripheral Component Interconnect Express (PCIe) link 710. USB/PCIe link 710 can include separate pins for the transmission of power and data (e.g., 2 pins, 3 pins, 4 or more pins). For example, power can be exchanged between mount 120 and patient monitor 150 via electrical line 720. Mount 120 can receive alternating current (AC) power from an external power source such as a wall power plug. The power can be passed through AC/direct current (DC) isolation component 701 (e.g., AC/DC converter having 4 kV AC isolation). A DC voltage V1 can be transmitted across electrical line 720 (e.g., 24 V DC). A DC/DC component 702 (e.g., DC/DC converter, non-isolated) can receive voltage V1 and output a reduced voltage V2 on electrical line 703 (e.g., 3.3 V). A controller circuit 704 and USB or PCIe Software (SW) 705 can be provided with reduced voltage V2 via electrical line 703. Controller circuit 704 can enable processor/processor core 154 to perform various functions as described herein. On one of the transmission pins, mount 120 and patient monitor 150 can share a common ground 730.

Some DC power from AC/DC component 701 also supplies power to components within mount 120. For example, a DC voltage on electrical line 720 can be passed to DC/DC component 706 (e.g., DC/DC converter, non-isolated). DC/DC component 706 can provide a reduced voltage level V3 (e.g., 3.3 V) along electrical line 707 to controller circuit 708 and USB or PCIe SW 709.

Data can be separately transmitted between mount 120 and patient monitor 150 via USB/PCIe link 710. In some variations, USB/PCIe link 710 can be a high speed (HS) USB interface that is a non-isolated link. An isolation component 712 within mount 120 can provide electrical isolation between mount 120 and front-end interfaces 711 (e.g., one or more physical input devices 221, 222, 223, 224, 225, 226). Isolation component 712 can provide a universal isolation point for the one or more physical input devices 221, 222, 223, 224, 225, 226 as opposed to requiring an individual isolation point for device. Similarly, patient monitor 150 can include an isolation component 713 that provides electrical isolation between patient monitor 150 and front-end interfaces 714. In some variations, electrostatic discharge (ESD) isolation component 715 and ESD isolation component 716 protect USB or PCIe PHY 717 and USB or PCIe PHY 718, respectively, from ESD potentially transmitted across USB/PCIe link 710. USB or PCIe SW 705 interfaces with USB or PCIe PHY 718 to encode and/or interpret data signals provided by or to USB and/or PCIe PHY 718. USB or PCIe SW 709 interfaces with USB or PCIe PHY 717 to encode and/or interpret data signals provided by and/or to USB or PCIe PHY 717.

Figure 8:
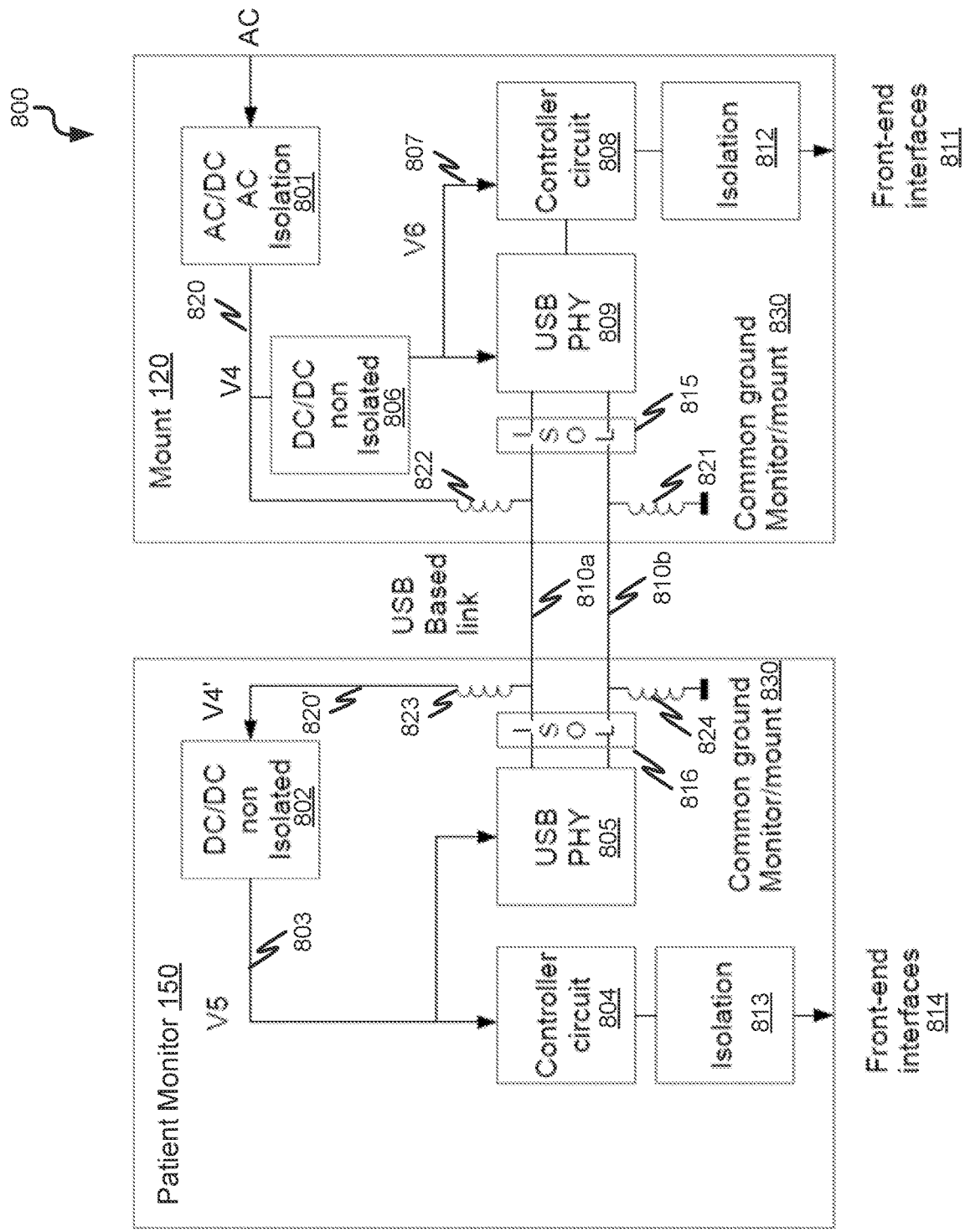
FIG. 8 depicts an example block diagram illustrating another example interchangeable transport medium of wired link(s)

FIG. 8 depicts an example block diagram 800 illustrating another example interchangeable transport medium 140 of wired link(s) 246. In some variations, wired link(s) 246 can be a USB based link made up of two pins 810a, 810b such as a super speed USB (e.g., 480 Mb/sec). USB based link can provide a capacitively coupled link (e.g., 100 nF) represented by capacitors 821, 822, 823, 824. Power can be provided to mount 120 and transmitted to patient monitor 150 through such capacitive coupling. For example, AC power can be provided to mount 120 from a power source such as a wall power plug. The power can be passed through AC/DC isolation component 801 (e.g., AC/DC converter having 4 kV AC isolation). Electrical line 820 can be coupled to capacitor 822. Electrical current can be transmitted through capacitors 822, 823 to electrical line 820'. A voltage V4' can be provided to a DC/DC component 802 coupled to electrical line 820'. A reduced voltage V5 can be provided on electrical line 803 (e.g., 3.3 V) to a controller circuit 804 and USB PHY 805. Controller circuit 804 can enable processor/processor core 154 to perform various functions as described herein. Mount 120 and patient monitor 150 can also share a common ground 830 that is external to the USB based link two-pin connection.

A DC voltage V4 can be transmitted across electrical line 820 (e.g., 24 V DC). A DC/DC component 806 (e.g., DC/DC converter, non-isolated) can receive the voltage V4. DC/DC component 806 can provide a reduced voltage V6 (e.g., 3.3V) along electrical line 807 to controller circuit 808 and USB PHY 809.

In order to transport power and data across USB based link (e.g., pins 810a, 810b), additional isolation components 815 and 816 (e.g., galvanic isolation) can be provided in both mount 120 and patient monitor 150, respectively. Isolation components 815 and 816 can generate an isolation voltage at least approximately twice as high as voltage V4 provided by AC/DC component 801 (e.g., 50 V). Additional isolation components 812 and 813 can provide electrical isolation between mount 120 and patient monitor 150 and front-end interfaces 811, 814, respectively.

Figure 9:
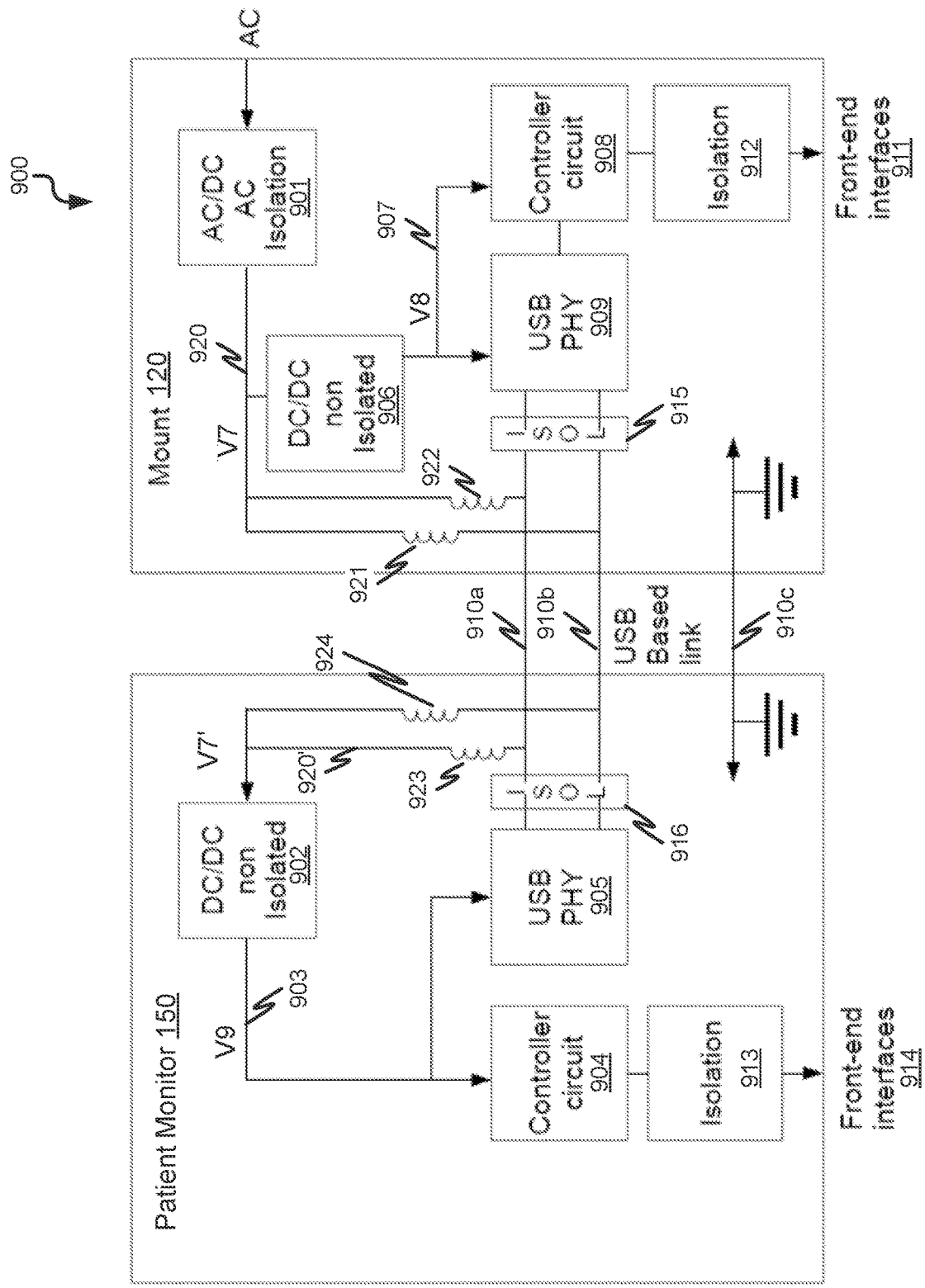
FIG. 9 depicts a block diagram illustrating another example interchangeable transport medium of wired link(s)

FIG. 9 depicts a block diagram 900 illustrating another example interchangeable transport medium of wired link(s) 246. In some variations, wired link(s) 246 can be a USB based link such as a super speed USB (e.g., 480 Mb/sec) having three pins (e.g., pins 910a, 910b, 910c). Pins 910a and 910b can transmit power and data between mount 120 and patient monitor 150. Pin 910c can provide for a common ground point between mount 120. A USB based link (e.g., pins 910a, 910b, 910c) can provide a capacitively coupled link (e.g., 100 nF) represented by capacitors 921, 922, 923, 924. Power can be provided to mount 120 and transmitted to patient monitor 150 through such capacitive coupling. For example, AC power can be provided to mount 120 from a power source such as a wall power plug. The power can be passed through AC/DC isolation component 901 (e.g., AC/DC converter having 4 kV AC isolation). A DC voltage V7 can be transmitted across electrical line 920 (e.g., 24 V DC). Electrical line 920 can be coupled to capacitor 922 and transmit electrical current through capacitor 923 to electrical line 920'. A voltage V7' can be provided to a DC/DC component 902 coupled to electrical line 920'. A reduced voltage (e.g., 3.3 V) V9 on electrical line 903 can be provided to a controller circuit 904 and USB PHY 905. Controller circuit 904 can enable processor/processor core 154 to perform functions as described herein. Mount 120 and patient monitor 150 can also share a common ground 930.

A DC/DC component 906 (e.g., DC/DC converter, non-isolated) can receive the voltage V7. DC/DC component 906 can provide a reduced voltage (e.g., 3.3 V) V8 along electrical line 907 to controller circuit 908 and USB PHY 909.

In order to transport power and data across USB based link 910, additional isolation components 915 and 916 (e.g., galvanic isolation) can be provided in both mount 120 and patient monitor 150, respectively. Isolation components 915 and 916 can generate an isolation voltage at least approximately twice as high as voltage V7 provided by AC/DC component 901 (e.g., 50 V). Additional isolation components 912 and 913 can provide electrical isolation between mount 120 and patient monitor 150 and front-end interfaces 911, 914, respectively.

Figure 10:
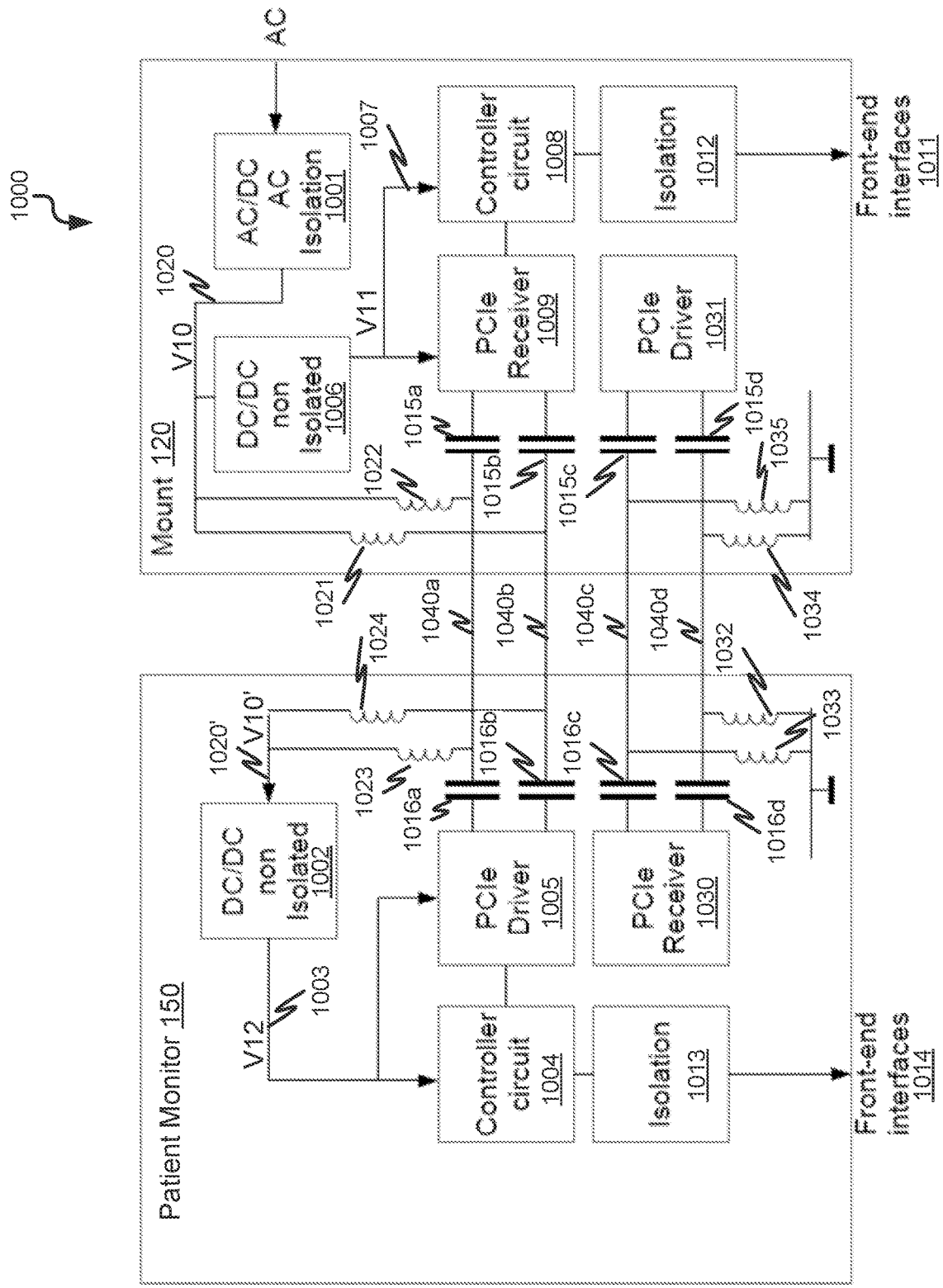
FIG. 10 depicts a block diagram illustrating another example interchangeable transport medium of wired link(s)

FIG. 10 depicts a block diagram 1000 illustrating another example interchangeable transport medium of wired link(s) 246. In some variations, wired link(s) 246 can include a PCIe link having a four-pin interface represented by electrical lines 1040a-d. Voltage can be provided across one differential pair of electrical lines (e.g., pins 1040a, 1040b) and ground connections can be provided across a second differential pair of electrical lines (e.g., pins 1040c, 1040d).

AC power can be provided to mount 120 from a power source such as a wall power plug. The power can be passed through AC/DC isolation component 1001 (e.g., AC/DC converter having 4 kV AC isolation). A DC voltage V10 can be transmitted across electrical line 1020 (e.g., 24 V DC). A DC/DC component I 006 (e.g., DC/DC converter, non-isolated) can receive the voltage V10. DC/DC component 1006 can provide a reduced voltage V11 (e.g., 3.3 V) along power line 1007 to controller circuit 1008 and PCIe receiver 1009.

Electrical line 1020 can be coupled to capacitor 1022 and transmit electrical current through capacitor 1023 to electrical line 1020'. A voltage V10' can be provided to a DC/DC component 1002 coupled to electrical line 1020'. A reduced voltage V12 (e.g., 3.3 V) on electrical line 1003 to a controller circuit 1004 and PCIe driver 1005. Controller circuit 1004 can enable processor/processor core 154 to perform functions as described herein.

Isolation components 1015a-1015d, 1016a-1016d (e.g., galvanic isolation) can be provided in both mount 120 and patient monitor 150, respectively. Additional isolation components 1012 and 1013 can provide electrical isolation between mount 120 and patient monitor 150 and front-end interfaces 1011, 1014, respectively. In addition to isolation, PCIe driver 1031 and PCIe receiver 1030 can be commonly grounded through capacitors 1032, 1033, 1034, 1035.

Figure 11:
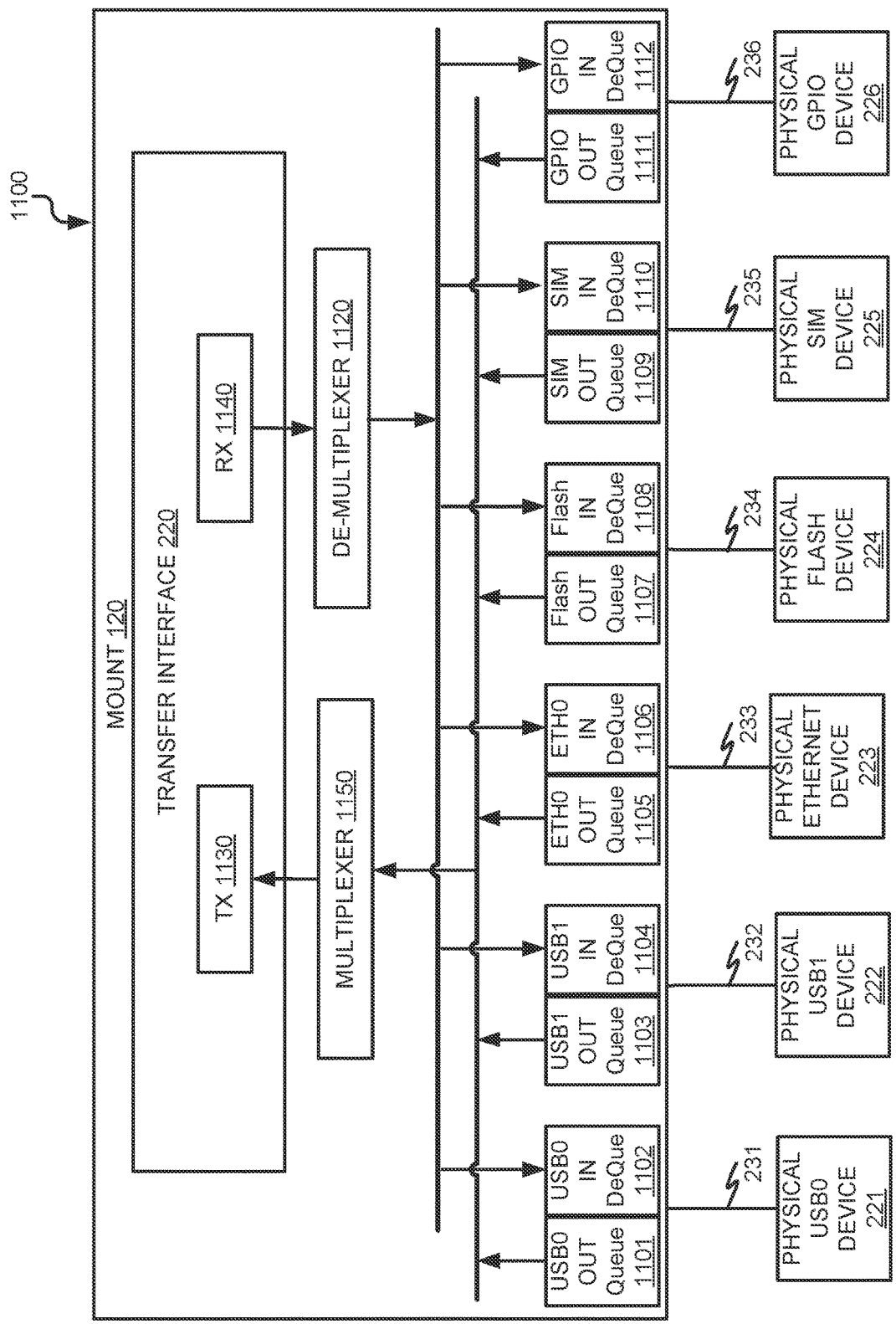
FIG. 11 depicts a block diagram illustrating example signal routing within mount.

FIG. 11 depicts a block diagram 1100 illustrating example signal routing within mount 120. Transport interface 220 can manage various signals communicated between mount 120 and patient monitor 150. For example, data coming from one or more physical input devices such as physical USB0 device 221, physical USB1 device 222, physical Ethernet device 223, physical flash drive 224, physical SIM device 225, and/or physical GPIO device 226 can be routed to a respective out queue (e.g., USB0 out queue 1101, USB1 out queue 1103, ETH0 out queue 1105, Flash out queue 1107, SIM out queue 1109, GPIO out queue 1111). The out queue data can be transmitted to a multiplexer 1150 for multiplexing of the various signals. Subsequently the signals can be transmitted to a transmission component TX 1130 of transfer interface 220 for prioritization as described in FIG. 2. Data received by mount 120 can be unpacked from a single data stream by transfer interface 220.

A receiving component RX 1140 can send data to a de-multiplexer 1120. De-multiplexer can separate and transmit signals (e.g., based on signal type) to an appropriate deque component (e.g., USB0 in queue 1102, USB1 in queue 1104, ETH0 in queue 1106, Flash in queue 1108, SIM in queue 1110, GPIO in queue 1112). Data can be transmitted back to one or more physical input devices such as physical USB0 device 221, physical USB1 device 222, physical Ethernet device 223, physical flash drive device 224, physical SIM device 225, and/or physical GPIO device 226 can be routed to a respective deque component (e.g., USB0 in queue 1102, USB1 in queue 1104, ETH0 in queue 1106, Flash in queue 1108, SIM in queue 1110, GPIO in queue 1112).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers.

A client and server are generally remote from each other and typically interact through a communication network. The relationship of client and server arises by virtue of computer programs running on the respective computers and having a client-server relationship to each other. The computing systems/devices can include a variety of devices including personal computers, mobile phones, tablet computers, and Internet-of-Things (IoT) devices.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "computer-readable medium" refers to any computer program product, apparatus and/or device, such as for example magnetic discs, optical disks, solid-state storage devices, memory, and Programmable Logic Devices (PLDs), used to provide machine instructions and/or data to a programmable data processor, including a computer-readable medium that receives machine instructions as a computer-readable signal. The term "computer-readable signal" refers to any signal used to provide machine instructions and/or data to a programmable data processor. The computer-readable medium can store such machine instructions non-transitorily, such as for example as would a non-transient solid-state memory or a magnetic hard drive or any equivalent storage medium. The computer-readable medium can alternatively or additionally store such machine instructions in a transient manner, for example, as would a processor cache or other random access memory associated with one or more physical processor cores.

To provide for interaction with a user, the subject matter described herein can be implemented on a computer having a display device (e.g., a CRT (cathode ray tube) or LCD (liquid crystal display) monitor) for displaying information to the user and a keyboard and a pointing device (e.g., a mouse or a trackball) and/or a touch-screen by which the user can provide input to the computer. Other kinds of devices can be used to provide for interaction with a user as well; for example, feedback provided to the user can be any form of sensory feedback (e.g., visual feedback, auditory feedback, and/or tactile feedback); and input from the user can be received in any form, including acoustic, speech, or tactile input.

In the descriptions above and in the claims, phrases such as "at least one of" or "one or more of" can occur followed by a conjunctive list of elements or features. The term "and/or" can also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations can be within the scope of the following claims.

The invention claimed is:

1. A system for use with a first physical device and a second physical device configured to provide data relating to a patient via a first data stream and a second data stream, respectively, wherein the first data stream comprises a first data type and the second data stream comprises a second data type and excludes the first data type, the system comprising:
 a mount module, including at least one processor, configured to be coupled to the first physical device and the second physical device, wherein the mount module is configured to (i) receive the first data stream and the second data stream, wherein the first data stream comprises physiological data derived from the patient as the first data type and the second data stream comprises non-physiological data as the second data type, (ii) apply different priority levels to each of the first physical device and the second physical device based on respective data types, including the first data type and the second data type, and (iii) generate a prioritized data stream comprising the first data stream and the second data stream based on the different priority levels assigned to both of the first physical device and the second physical device, wherein, when generating the prioritized data stream, data provided by the first data stream is given a higher priority over data provided by the second data stream, wherein the mount module comprises a first transfer interface configured to emulate operational characteristics of the first data stream received from the first physical device and the second data stream received from the second physical device by translating the first data stream and the second data stream into compatible signal representations for transport, wherein the operational characteristics include at least one: device signals, control lines, or protocols within the first data stream and the second data stream;
 a patient monitoring device, including at least one processor, configured to receive the prioritized data stream via a single data connection and to unpack the prioritized data stream into virtual representations of the first data stream and the second data stream, wherein the virtual representations emulate operational characteristics of the first physical device and the second physical device; and
 an interchangeable transport medium module comprising a virtualized connection arranged between the mount module and the patient monitoring device, wherein the virtualized connection comprises a plurality of virtual local area networks (VLANs), wherein the VLANs have different priorities according to the different priority levels, the interchangeable transport medium module configured to transport the first data stream using a first VLAN of the VLANs and the second data stream using a second VLAN of the VLANs of different priorities, wherein the prioritized data stream is transported as compatible signal representations via the single data connection.

2. The system of claim 1, wherein the priority level assigned to the first physical device is higher than the priority level assigned to the second physical device.

3. The system of claim 2, wherein the mount module is configured to limit a throughput rate at which the second data stream is provided into the prioritized data stream according to a throughput rate threshold.

4. The system of claim 1, wherein an operating system performs assignment of the different priority levels to the first physical device and the second physical device.

5. The system of claim 1, wherein the first transfer interface is configured to emulate the operational characteristics by translating the first data stream and the second data stream into the compatible signal representations for transport using the interchangeable transport medium module.

6. The system of claim 1, wherein the at least one: device signals, control lines, or protocols is within the first data stream and the second data stream.

7. The system of claim 6, wherein the mount module further comprises a multiplexer configured to queue the first data stream and the second data stream for generation of the prioritized data stream according to the different priority levels.

8. The system of claim 1, wherein the patient monitoring device comprises a second transfer interface configured to split the prioritized data stream into the virtual representations of the first data stream and the second data stream, wherein the second transfer interface is further configured to process the virtual representations of the first data stream and the second data stream, generate a prioritized response data stream based on the different priority levels, and transmit the prioritized response data stream to the mount module.

9. The system of claim 8, wherein the mount module further comprises a de-multiplexer configured to deque the prioritized response data stream into a first response data stream and a second response data stream according to the different priority levels.

10. The system of claim 1, wherein the second physical device is an Ethernet device configured to communicate with a hospital data network.

11. The system of claim 1, wherein the first physical device is a physiological data acquisition device coupled to the patient, the first physical device being configured to obtain physiological data from the patient and provide the physiological data as the first data type transmitted to the mount module in the first data stream.

12. The system of claim 11, wherein the second data stream comprises network data as the second data type.

13. The system of claim 1, wherein the patient monitoring device is configured to unpack the prioritized data stream such that the data provided by the first data stream is unpacked with priority over the data provided by the second data stream.

14. The system of claim 1, wherein the mount module generates the prioritized data stream by combining the first data stream and the second data stream into a single data stream transmitted by the single data connection,
wherein the prioritized data stream is a continuous stream of data with data of the first data stream and data of the second data stream intermixed over time.

15. The system of claim 1, wherein:
the patient monitoring device includes a first virtual device configured to emulate the first physical device, receive the virtual representation of the first data stream, and provide the virtual representation of the first data stream in a first emulated data stream to a first physical output port of the patient monitoring device, and
the patient monitoring device includes a second virtual device configured to emulate the second physical device, receive the virtual representation of the second data stream, and provide the virtual representation of the second data stream in a second emulated data stream to a second physical output port of the patient monitoring device.

16. The system of claim 15, wherein:
the first virtual device is configured to emulate at least one of device signals, control lines, or protocols of the first physical device based on the virtual representation of the first data stream, and
the second virtual device is configured to emulate at least one of device signals, control lines, or protocols of the second physical device based on the virtual representation of the second data stream.

17. The system of claim 1, wherein the mount module is configured to supply power to the patient monitoring device via a power connection.

18. An apparatus for use with a first physical device, a second physical device, and a patient monitoring device, the first physical device and the second physical device being configured to provide data relating to a patient via a first data stream and a second data stream, respectively, wherein the first data stream comprises a first data type and the second data stream comprises a second data type and excludes the first data type, the apparatus comprising:
a mount module, including at least one processor, having a first input port coupled to the first physical device and a second input port coupled to the second physical device, wherein the mount module is configured to (i) receive the first data stream and the second data stream, wherein the first data stream comprises physiological data derived from the patient as the first data type and the second data stream comprises non-physiological data as the second data type, (ii) apply different priority levels to each of the first physical device and the second physical device based on respective data types, including the first data type and the second data type, and (iii) generate a prioritized data stream comprising the first data stream and the second data stream based on the different priority levels assigned to the first physical device and the second physical device, wherein, when generating the prioritized data stream, data provided by the first data stream is given a higher priority over data provided by the second data stream, wherein the mount module comprises a first transfer interface configured to emulate operational characteristics of the first data stream received from the first physical device and the second data stream received from the second physical device by translating the first data stream and the second data stream into compatible signal representations for transport, wherein the operational characteristics include at least one: device signals, control lines, or protocols within the first data stream and the second data stream; and
an interchangeable transport medium module comprising a virtualized connection arranged between the mount module and the patient monitoring device, wherein the virtualized connection comprises a plurality of virtual local area networks (VLANs), wherein the VLANs have different priorities according to the different priority levels, and configured to transport the first data stream using a first VLAN of the VLANs and the second data stream using a second VLAN of the VLANs of different priorities, wherein the prioritized data stream is transported as compatible signal representations via a single data connection,
wherein the patient monitoring device includes at least one processor and is configured to receive the prioritized data stream via the single data connection and unpack the prioritized data stream into virtual representations of the first data stream and the second data stream and wherein the virtual representations emulate the operational characteristics of the first physical device and the second physical device.

19. A method for prioritizing data streams according to different priority levels, the method comprising:
receiving, by a mount module, a first data stream from a first physical device, wherein the first data stream comprises a first data type;
receiving, by the mount module, a second data stream from a second physical device, wherein the second data stream comprises a second data type and excludes the first data type, wherein the first data stream comprises physiological data derived from the patient as the first data type and the second data stream comprises non-physiological data as the second data type;
applying the different priority levels to each of the first physical device and the second physical device based on respective data types, including the first data type and the second data type;
generating, by the mount module, a prioritized data stream comprising the first data stream and the second data stream that is based on the different priority levels assigned to both of the first physical device and the second physical device, wherein data provided by the first data stream is given a higher priority over data provided by the second data stream, wherein the mount module comprises a first transfer interface configured to emulate operational characteristics of the first data stream received from the first physical device and the second data stream received from the second physical device by translating the first data stream and the second data stream into compatible signal representations for transport, wherein the operational characteristics include at least one: device signals, control lines, or protocols within the first data stream and the second data stream;
transporting, by an interchangeable transport medium module comprising a virtualized connection, data streams of different priorities, wherein the virtualized connection comprises a plurality of virtual local area networks (VLANs), wherein the VLANs have different priorities according to the different priority levels, wherein the transporting comprises transporting the first data stream using a first VLAN of the VLANs and the second data stream using a second VLAN of the VLANs of different priorities;

receiving, by the patient monitoring device, the prioritized data stream via the single data connection; and unpacking, by the patient monitoring device, the prioritized data stream into virtual representations of the first data stream and the second data stream, wherein the virtual representations emulate the operational characteristics of the first physical device and the second physical device.

\* \* \* \* \*